United States Patent [19]

Kita et al.

[11] Patent Number: 4,962,205
[45] Date of Patent: Oct. 9, 1990

[54] METHOD FOR TRANSPORTATION AND STORAGE OF N-PHENYL MALEIMIDE IN MOLTEN FORM

[75] Inventors: Yuichi Kita, Akashi; Kazuo Kishino, Himeji; Akio Fukui, Fujisawa, all of Japan

[73] Assignee: Nippon Shokubai Kagaku Kogyo, Co., Ltd., Osaka, Japan

[21] Appl. No.: 392,482

[22] Filed: Aug. 11, 1989

[51] Int. Cl.$^5$ ........................................ C07D 207/448
[52] U.S. Cl. .................................................... 548/549
[58] Field of Search ........................................ 548/549

[56] References Cited

U.S. PATENT DOCUMENTS 1,894,969  1/1933  Wood ................................. 514/425
4,493,920  1/1985  Le-Khac .
4,500,719  2/1985  Oba et al. ............................ 548/549
4,623,734  11/1986 Kita et al. .

FOREIGN PATENT DOCUMENTS 2132854   7/1987  Japan ................................... 548/549
62-25791  11/1987 Japan .
1041027   9/1966  United Kingdom .

Primary Examiner—David B. Springer
Attorney, Agent, or Firm—Omri M. Behr

[57] ABSTRACT

Method for the transportation or storage of N-phenyl maleimide, which method comprises mixing N-phenyl maleimide with maleic anhydride in a ratio of 1 to 90 parts by weight of N-phenyl maleimide to 99 to 10 parts by weight of maleic anhydride and handling the resultant mixture in a molten state in the presence of a polymerization inhibitor, and a composition of liquid state.

4 Claims, No Drawings

METHOD FOR TRANSPORTATION AND STORAGE OF N-PHENYL MALEIMIDE IN MOLTEN FORM

BACKGROUND OF THE INVENTION

1. Field of the Invention

This invention relates to a method for the transportation and storage of N-phenyl maleimide in a liquid state and to a composition to be used therefor.

2. Description of the Prior Art

N-phenyl maleimide is a compound useful as raw material for synthetic resins, medicines, and agricultural chemicals, for example. The N-phenyl maleimide has been heretofore handled generally in such forms as powder, flakes, and tablets. These forms of N-phenyl maleimide contain fine powder of N-phenyl maleimide. The N-phenyl maleimide in a solid state, particularly in the process of transportation, undergoes gradual comminution and eventually gives rise to a large amount of the fine powder of N-phenyl maleimide.

The N-phenyl maleimide itself is stimulative to the human body. Particularly when the fine powder thereof is inhaled, it stimulates the nasal cavity and the throat and consequently incites coughs and sneezes. When this powder is suffered to adhere to and remain on the skin, it causes inflammation of the affected area of the skin. Any person called upon to handle N-phenyl maleimide of the kind containing such a fine powder as mentioned above, therefore, must pay close attention to preventing the compound from adhering to the skin to the fullest possible extent. Immense labor is expended, therefore, for preventing the N-phenyl maleimide in transit from producing fine powder and, after completion of the transportation, for divesting the transported N-phenyl maleimide of the fine powder produced at all during the transportation.

In most cases, a solid substance to be transported is packed in paper bags, steel drums, and returnable containers. During the work of packing, therefore, the exposure of the worker's body to the N-phenyl maleimide is inevitable and the adhesion of the fine powder of N-phenyl maleimide to the body cannot be avoided. Further, an attempt at transporting a solid substance through the medium of a pipeline with a view to keeping handlers from exposure to the solid substance is difficult basically and the solid substance is so mischievous as to induce occlusion of the pipeline. For stable transportation of the solid substance through the pipeline, therefore, harsh restrictions are imposed on the transportation as to shape, size, and specific gravity of the solid substance. It is only logical to conclude, therefore, that the method for transporting or conveying solid N-phenyl maleimide at normal room temperature entails various difficulty problems. This conclusion holds good with the method for storing this substance under the same conditions.

The conventional methods for transportation and storage of N-phenyl maleimide encounter numerous problems. Especially the handling of this compound on a commercial scale entails many disadvantages.

An object of this invention, is to provide a novel method for transportation or storages of N-phenyl maleimide and a composition to be used therefor.

Another object of this invention is to provide a safe and simple method for transportation or storage of N-phenyl maleimide which has no possibility of inducing the occurrence of fine powder of the compound during the course of transportation or storage and a composition to be used therefor.

SUMMARY OF THE INVENTION

These objects are accomplished by a method for the transportation or storage of N-phenyl maleimide, which method comprises mixing N-phenyl maleimide with maleic anhydride in a ratio of 1 to 90 parts by weight of N-phenyl maleimide to 99 to 10 parts by weight of maleic anhydride and handling the resultant mixture in the presence of a polymerization inhibitor in a molten state.

These objects are also accomplished by a N-phenyl maleimide composition suitable for transportation or storage, which N-phenyl maleimide composition comprises a molten mixture containing 1 to 90 parts by weight of N-phenyl maleimide and 99 to 10 parts by weight of maleic anhydride and incorporating therein a polymerization inhibitor.

our study had revealed that when N-phenyl maleimide is mixed with maleic anhydride, it forms a mixture possessing a very low melting point and, therefore, can be handled easily in a liquid state at a relatively low temperature.

It has been also ascertained to unexpectedly that N-phenyl maleimide, in the mixture thereof with maleic anhydride, is stable to resist polyemrization in the presence of a polymerization inhibitor.

They have consequently found that when N-phenyl maleimide and maleic anhydride are mixed to form a mixed liquid and the mixed liquid is transported, it can be handled easily without inducing the occurrence of fine powder at all. This invention has been accomplished as the result.

N-phenyl maleimide is used as a heatresistance enhancer for such copolymers of maleic anhydride as maleic anhydride-styrene copolymer and maleic anhydride-modified polyolefins.

U.S. Pat. No. 4,493,920 discloses a blend of a styrene ternary copolymer containing maleic anhydride and N-phenyl maleimide with a polycarbonate. The gravimetric ratio or maleic anhydride to N-phenyl maleimide in the ternary copolymer is in the range of 30:70 to 70:30.

Japanese Patent Laid-Open Sho 62(1987)-257,913 discloses a ternary copolymer which comprises an α-olefin, maleic anhydride, and N-phenyl maleimide and which is useful for adhesive agent, coating agent, and paper additive excellent in heatresistance and waterresistance. The gravimetric ratio of maleic anhydride to N-phenyl maleimide in the ternary copolymer is in the range of 60:40 to 90:10.

Various polymers using maleic anhydride and N-phenyl maleimide as two additive components have been finding extensive utility. In these copolymers, maleic anhydride and N-phenyl maleimide are generally used in such amounts that the gravimetric ratio of maleic anhydride:N-phenyl maleimide falls in the range of 10:90 to 99:1.

N-phenyl maleimide, even in the presence of a polymerization inhibitor, is unstable at a temperature exceeding the melting point (89° C.) and succumbs to gradual polymerization. The development of means for transporting or storing N-phenyl maleimide at a low temperature below the melting point in a liquid state incapable of producing fine powder detrimental to the human body, therefore, is significant from the technological point of view.

This invention has originated in our newly acquired knowledge that, as demonstrated in the referential example cited herein below, a molten mixture of N-phentl maleimide with maleic anhydride possesses a notably low melting point and can be handled in a liquid state.

To be specific, the substitution of N-phenyl maleimide for part of maleic anhydride permits a polymer to enjoy enhanced heatproofness.

When N-phenyl maleimide is prepared in the form of a mixture with maleic anhydride, it can be easily handled in a liquid state. The mixture, therefore, can be readily transported or conveyed and safely stored without being directly exposed to handlers and can preclude the occurrence of fine powder. In the synthesis of a resin, since the maleic anhydride constitutes itself one of the components of copolymer other than N-phenyl maleimide, the mixture of N-phenyl maleimide with maleic anhydride manifests many advantages such as the usability thereof in its unaltered form in the polymerization reaction.

Thus, in the transportation of N-phenyl maleimide, the method of handling this compound in the form of a mixture thereof with maleic anhydride may well be called an ideal measure.

EXPLANATION OF THE PREFERRED EMBODIMENT

This invention is directed to a method for the transportation or storage of N-phenyl maleimide characterized by handling the N-phenyl maleimide in the form of a mixture thereof with maleic anhydride in the presence of a polymerization inhibitor.

The polymerization inhibitors which are usable in the handling of N-phenyl maleimide in the form of a mixture thereof with maleic anhydride include methoxybenzoquinone; p-methoxyphenol; phenothiazine; hydroquinone; alkylated diphenylamines; methylene blue; 4-t-butyl catechol; alkyl hydroquinones such as 2-t-butyl hydroquinone and 2,5-di-t-butyl hydroquinone; dialkyl dithiocarbamates such as zinc dimethyldithiocarbamate, copper dimethyldithiocarbamate, and copper dibutyldithiocarbamate; copper salicylate; thiodipropionic ester, mercaptobenzoimidazole; alkyl phenols such as triphenyl phosphites and 2,4-dimethyl-6-t-butylphenol; alkyl bisphenols; 2,4-bis(n-octylthio-6-(4-hydroxy-3,5-di-6-butylanilino)-1,3,5-triazine; and hindered phenols such as 2,2'-thiobis-(4-methyl-6-t-butyl-phenol), 4,4'-thiobis-(6-t-butyl-m-cresonl), and triethylene glycol bis-[3-(3-6-butyl-5-methyl-4-hydroxyphenyl)propionate], for example. These are not the only polymerization inhibitors that are available for this invention. The amount of such a polymerization inhibitors to be used is in the range of 0.0001 to 0.5% by weight, preferably 0.001 to 0.1% by weight, based on the amount of the mixture N-phenyl maleimide with maleic anhydride. The particular kind of this polymerization inhibitor to be used herein is selected in due consideration of the kind of polymer to be produced, the method of polymerization to be involved, the kind of initiator to be used, for example.

The temperature at which N-phenyl maleimide is mixed with maleic anhydride is desired to exceed the melting point of maleic anhydride. The melting of this mixture is carried out at a temperature in the range of 60° to 100° C., preferably 70° to 90° C. The molten mixture is transported or stored at a temperature in the range of 35° to 100° C., preferably 40° C. to 90° C.

Incidentally, thr melting of the mixture can be effected basically by any of the known methods. It may be effected by pouring maleic anhydride into N-phenyl maleimide. Preferably, however, it is carried out by pouring N-phenyl maleimide into maleic anhydride.

The mixing ratio of N-phenyl maleimide to maleic anhydride (by weight) is in the range of 1:99 to 90:10, preferably 10:90 to 80:20, most preferably 20:80 to 60 to 40. This is because the mixed liquid of N-phenyl maleimide and maleic anhydride can be handled in the neighborhood of normal room temperature when the concentration of N-phenyl maleimide is in the range of 20 to 60% by weight.

Now, this invention will be described more specifically below with reference to working examples.

Example 1

In a flask having an inner volume of 500 ml and provided with a stirrer and a condenser, 100 g of maleic anhydride and 10 mg of p-methoxy phenol were placed. The internal temperature of the flask was kept at 50° C. by adjusting the temperature of the water bath. When the contents of the flask were stirred and 100 g of N-phenyl maleimide crystals 99.5% by weight in purity were added thereto, the N-phenyl maleimide crystals were quickly dissolved to give rise to a preferably clear yellow mixed liquid of maleic anhydrous.

Then, the contents of the flask were kept at an internal temperature of 50° C. for 30 days. The clarity of the liquid in the flask remained intact even after 30 days standing. When this liquid was tested for N-phenyl maleimide content by high speed liquid chromatography, this content was found to be 50% by weight, indicating total absence of polymerization.

Example 2

A perfectly clear yellow mixed liquid of maleic anhydride was obtained by repeating the procedure of Example 1, except that 50 mg of p-tert-butyl catechol was used in the place of 10 mg of p-methoxy phenol.

Then, the contents of the flask were kept at an internal temperature of 50° C. for 30 days. The clarity of the liquid in the flask remained intact even after 30 days standing. When this liquid was tested for N-phenyl maleimide content by high speed liquid chromatography, this content was found to be 50% by weight, indicating total absence of polymerization.

Control 1

When the procedure of Example 1 was faithfully repeated, except that the use of p-methoxy phenol was omitted, the mixed liquid turned into a reddish brown viscous liquid after 30 days standing at 50° C.

When this liquid was tested for N-phenyl maleimide content by high-speed liquid chromatography, the content was found to be 32% by weight, clearly indicating that the liquid was degenerated.

Examples 3 to 9

In the same apparatus as used in Example 1, 80 g of maleic anhydride and 120 g of N-phenyl maleimide crystals were mixed and the mixture was kept at 50° C. for 30 days in the presence of a varying polymerization inhibitor.

After the standing, the mixed liquid was tested for N-phenyl maleimide content by high-speed liquid chromatography to determine the residual ratio of N-phenyl maleimide. The results were as shown in Table 1.

TABLE 1

| Example | Polymerization inhibitor | Amount (mg) | Residual ratio of N-phenyl maleinide (%) |
|---|---|---|---|
| 3 | 2,4-dimethyl-6-t-butyl phenol | 100 | 100 |
| 4 | 2,5-di-t-butyl hydroquinone | 10 | 100 |
| 5 | 4,4'-thiobis-(6-t-butyl methacresol) | 30 | 100 |
| 6 | 2,2'-thiobis-(4-methyl-6-t-butyl phenol) | 200 | 100 |
| 7 | disteary-3,3'-thiodi-propionate | 50 | 100 |
| 8 | TGBP | 100 | 100 |
| 9 | BOHT | 50 | 100 |

(Note)
TGBP: triethylene glycol-bis[3-(3-t-butyl-5-methyl-4-hydroxyphenyl) propionate]
BOHT: 2,4-bis(n-octylthio)-6-(4-hydroxy-3,5-di-t-butyl anilino)-1,3,5-triazine Referential Example 1

Various mixture of N-phenyl maleimide with maleic anhydride were tested for melting points. The results were as shown below.

| N-phenyl maleimide (% by weight) | Maleic anhydride (% by weight) | Melting point (°C.) |
|---|---|---|
| 100 | 0 | 89 |
| 80 | 20 | 68 |
| 60 | 40 | 49 |
| 40 | 60 | 32 |
| 20 | 80 | 44 |
| 0 | 100 | 53 |

What is claimed is:

1. A method of providing N-phenyl maleimide in a form suitable for transportation or storage, which comprises melting maleic anhydride in the presence of a polymerization inhibitor, adding thereto N-phenyl maleimide and maintaining the temperature of the mixture at a temperature sufficient to maintain said mixture in a molten state in the range of 35° to 100° C., wherein the ratio of maleic anhydride to N-phenyl maleimide lies in the range of 1 to 90:99 to 10 and the amount of polymerization inhibitor is in the range of 0.0001 to 0.5% by weight, based on said mixture of N-phenyl maleimide with maleic anhydride.

2. A method according to claim 1 wherein said mixture comprises 10 to 80 parts by weight of N-phenyl maleimide and 90 to 20 parts by weight of maleic anhydride.

3. A molten N-phenyl maleimide composition comprising molten maleic anhydride in the presence of a polymerization inhibitor and N-phenyl maleimide at the temperature of the mixture being sufficient to maintain said mixture in a molten state in the range of 35° to 100° C., wherein the ratio of maleic anhydride to N-phenyl maleimide lies in the range of 1 to 90:99 to 10 and the amount of polymerization inhibitor is in the range of 0.0001 to 0.5% by weight, based on said mixture of N-phenyl maleimide with maleic anhydride.

4. A composition according to claim 3, wherein said mixture comprises 10 to 80 parts by weight of N-phenyl maleimide and 90 to 20 parts by weight of maleic anhydride.

* * * * *